United States Patent
Fujita

(10) Patent No.: US 9,983,177 B2
(45) Date of Patent: May 29, 2018

(54) AUTOSAMPLER AND LIQUID CHROMATOGRAPH

(71) Applicant: SHIMADZU CORPORATION, Kyoto-shi, Kyoto (JP)

(72) Inventor: Takaaki Fujita, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 95 days.

(21) Appl. No.: 15/062,627

(22) Filed: Mar. 7, 2016

(65) Prior Publication Data
US 2016/0274069 A1  Sep. 22, 2016

(30) Foreign Application Priority Data
Mar. 16, 2015  (JP) .................. 2015-052410

(51) Int. Cl.
| | |
|---|---|
| *G01N 30/20* | (2006.01) |
| *G01N 30/24* | (2006.01) |
| *G01N 30/32* | (2006.01) |
| *G01N 30/34* | (2006.01) |
| *G01N 1/00* | (2006.01) |

(52) U.S. Cl.
CPC ............ *G01N 30/20* (2013.01); *G01N 30/24* (2013.01); *G01N 30/32* (2013.01); *G01N 30/34* (2013.01); *G01N 2001/002* (2013.01); *G01N 2030/202* (2013.01); *G01N 2030/324* (2013.01)

(58) Field of Classification Search
CPC ........................................ G01N 30/20
USPC ............................................. 73/61.55
See application file for complete search history.

(56) References Cited

U.S. PATENT DOCUMENTS

| | | | |
|---|---|---|---|
| 2007/0251302 A1* | 11/2007 | Iwata | G01N 30/20 73/61.56 |
| 2011/0209532 A1 | 9/2011 | Maeda | |
| 2013/0014597 A1* | 1/2013 | Yasunaga | G01N 30/24 73/863.01 |
| 2013/0067997 A1 | 3/2013 | Ebsen et al. | |

FOREIGN PATENT DOCUMENTS

| | | |
|---|---|---|
| CN | 102253150 A | 11/2011 |
| JP | 2001-255316 A | 9/2001 |

OTHER PUBLICATIONS

Office Action dated Mar. 13, 2017, issued in counterpart Chinese Patent Application No. 201610041484.3, with English translation. (19 pages).

* cited by examiner

*Primary Examiner* — Manish S Shah
*Assistant Examiner* — Jean Morello
(74) *Attorney, Agent, or Firm* — Westerman, Hattori, Daniels & Adrian, LLP

(57) ABSTRACT

An autosampler according to an embodiment includes a sampling channel including a movable needle at a tip, and a switching valve, including a plurality of ports, for switching the connection state between the ports by switching the position of a rotor by rotating the rotor. The rotor of the switching valve includes an injecting position in which a delivery port and a sampling port are communicated and an injection port and an analysis port are communicated, a purging position in which the delivery port and the sampling port are communicated and the injection port and a drain port are communicated, and a loading position in which the delivery port and the analysis port are communicated.

7 Claims, 6 Drawing Sheets

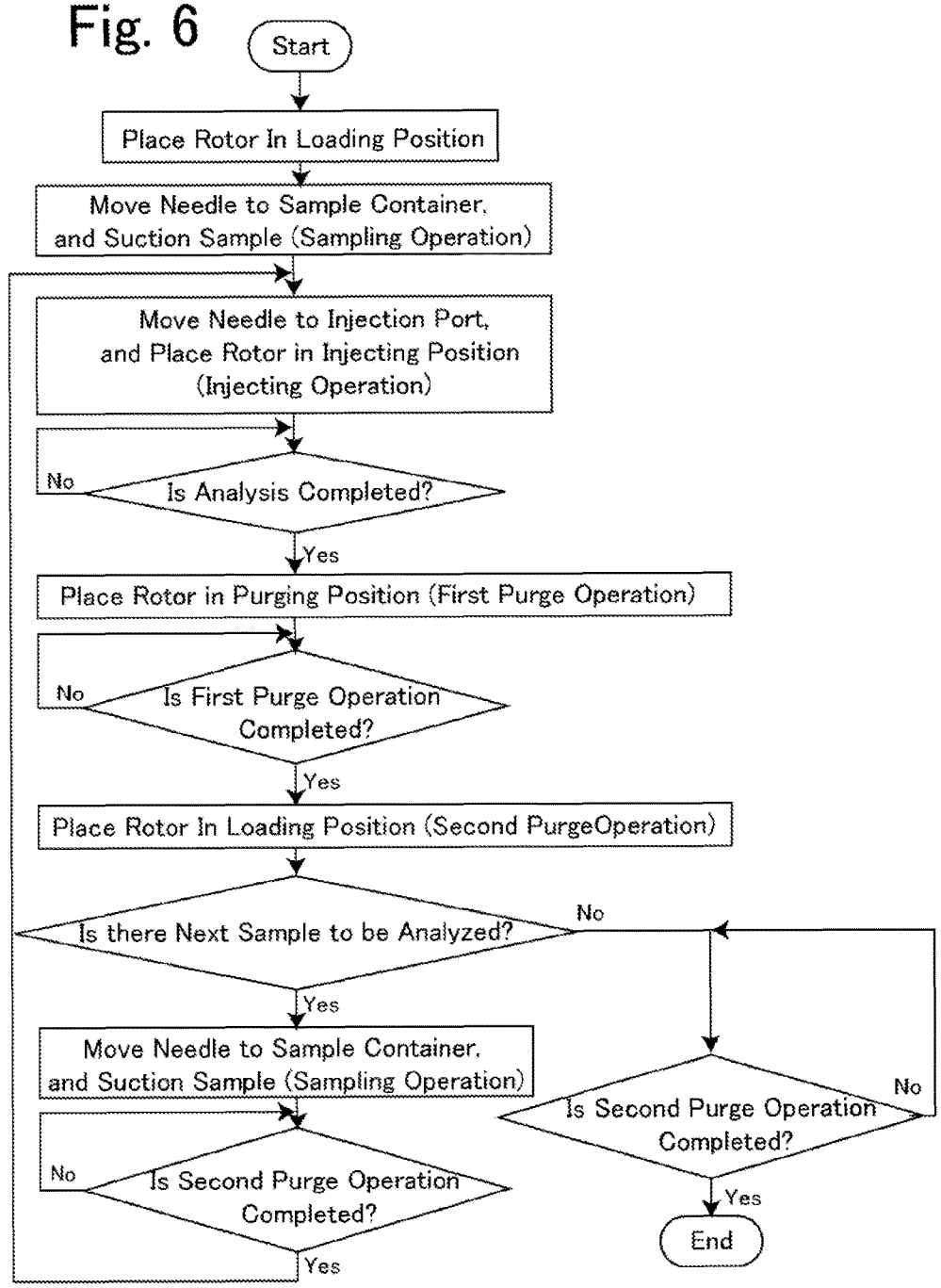

_US 9,983,177 B2_

AUTOSAMPLER AND LIQUID CHROMATOGRAPH

BACKGROUND OF THE INVENTION

1. Field of the Invention

The present invention relates to an autosampler for collecting a sample contained in a sample container by using a needle and for injecting the sample into an analysis channel provided with an analytical column and a detector, and a liquid chromatograph provided with the autosampler.

2. Description of the Related Art

A liquid chromatograph may use an autosampler of a total-volume injection method as an autosampler for injecting a sample into an analysis channel provided with an analytical column and a detector. An autosampler of the total-volume injection method performs analysis by retaining a sample taken in from a needle tip in a sample loop, inserting the needle tip into an injection port, and switching a channel structure by a switching valve so as to cause the sample loop to be present between a delivery device for delivering a mobile phase and the analytical column to thereby introduce the sample to the analytical column by the mobile phase from the delivery device (see JP 2001-255316 A).

In the case of analyzing a sample containing several components by a liquid chromatograph, gradient analysis may be used according to which the components of a mobile phase are changed stepwise (over time) so as to cause a component with a long retention time in an analytical column to be eluted in a short time while maintaining the separation performance for a component with a short retention time.

SUMMARY OF THE INVENTION

In the case of successively performing gradient analysis by a liquid chromatograph provided with an autosampler of the total-volume injection method, the entire channel after the previous analysis is filled with a mobile phase whose components have been changed in gradient, and thus, the mobile phase components in the channel have to be returned to the state before the gradient start before the next analysis is started.

Accordingly, a task of returning the components of the mobile phase in all of the channels including a sample loop to the components at the time of start of gradient by delivering, by a delivery device, a mobile phase with components before the start of gradient to an analytical column side through the sample loop is performed in a state where a needle is inserted in an injection port. While this task is being performed, the needle cannot be pulled out from the injection port, and thus, an operation of pulling out the needle from the injection port and collecting the next sample is performed after the task is completed. Accordingly, it takes a long time from the end of analysis of a sample to when analysis of the next sample can be started.

Accordingly, the present invention has its object to reduce the time from the end of analysis of a sample to when analysis of the next sample can be started.

An embodiment of an autosampler according to the present invention includes a sampling channel including, at a tip, a movable needle for performing suction and discharge of a sample, and also includes a sample loop for retaining a liquid taken in from the needle tip, and a switching valve. The switching valve includes a delivery port to which a delivery device for delivering a mobile phase is connected, a sampling port to which a base end of the sampling channel is connected, an injection port that is connected to the sampling channel by insertion of the tip of the needle, an analysis port to which an analysis channel provided with an analytical column is connected, a drain port that leads to a drain, and a rotor including a groove for communicating between the ports, the switching valve being for switching a connection state between the ports by switching a position by rotating the rotor. The rotor of the switching valve includes an injecting position in which the delivery port and the sampling port are communicated and the injection port and the analysis port are communicated, a purging position in which the delivery port and the sampling port are communicated and the injection port and the drain port are communicated, and a loading position in which the delivery port and the analysis port are communicated.

According to the embodiment of the autosampler of the present invention, the rotor of the switching valve includes the injecting position, the purging position, and the loading position as described above, and thus, by placing the rotor of the switching valve in the purging position after analysis of a sample is completed, replacement of the mobile phase in the sampling channel may be performed separately from the analysis channel. The channel resistance of the sampling channel is smaller than that of the analysis channel including the analytical column, and thus, the mobile phase may be delivered at a higher flow rate than in the analysis channel. Accordingly, the mobile phase in the sampling channel may be swiftly replaced. By switching the rotor of the switching valve to the loading position after replacement of the mobile phase in the sampling channel is completed, the delivery device and the analysis channel are communicated, and the sampling channel is separated from the delivery device. The next sample may be collected while the mobile phase in the analysis channel is being replaced. Accordingly, the time from the end of analysis to when the next analysis can be started is reduced compared to a conventional case.

An embodiment of a liquid chromatograph according to the present invention includes an analysis channel including an analytical column for separating a sample into components and a detector for detecting a sample component separated by the analytical column, a delivery device for supplying a mobile phase to the analysis channel, and the above-described autosampler, present between the delivery device and the analysis channel, for introducing a sample into the analysis channel.

The embodiment of the liquid chromatograph according to the present invention includes the autosampler described above, and thus, the time from end of analysis of a sample to when analysis of the next sample can be performed is reduced compared to a conventional case, and the overall time required at the time of successively analyzing a plurality of samples may be reduced.

BRIEF DESCRIPTION OF THE DRAWINGS

FIG. 6 is a flow chart showing a sample analysis operation according to the present example.

DETAILED DESCRIPTION OF THE INVENTION

Figure 1:
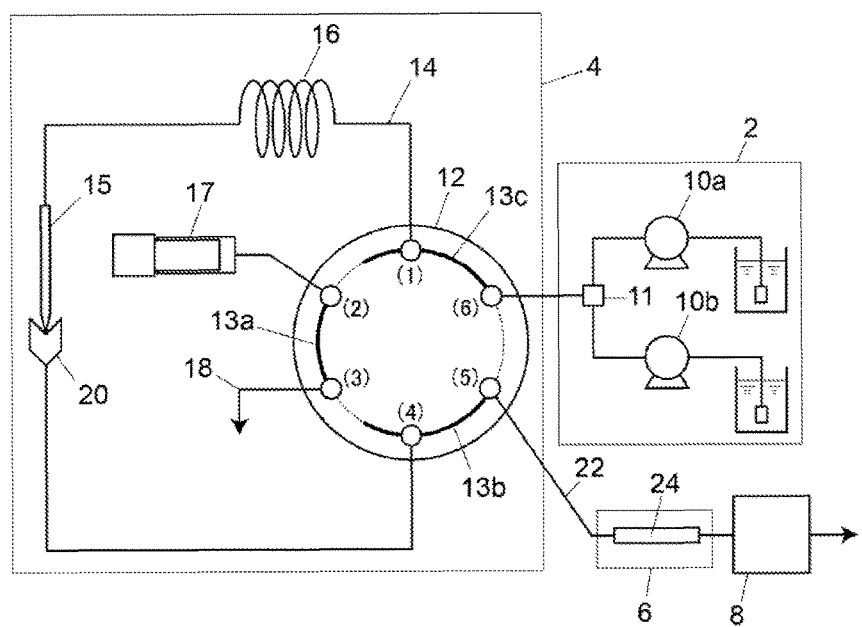
FIG. 1 is a channel structure diagram schematically showing an example of a liquid chromatograph.

According to a preferred embodiment of an autosampler, a syringe pump for performing suction and discharge of a liquid is further included, and a switching valve includes a syringe port leading to the syringe pump, and when a rotor is in a loading position, a sampling port and the syringe port are communicated with each other. Accordingly, when purging of a mobile phase inside an analysis channel is being performed by communicating between a delivery device and the analysis channel, a sample may be taken in from a needle tip by communicating between a sampling channel and the syringe pump.

As the switching valve of the embodiment of the autosampler, a 6-way valve whose ports are arranged on the same circumference may be used. In this case, a delivery port and a sampling port are arranged adjacent to each other, an analysis port is arranged adjacent to the delivery port on the other side of the sampling port, an injection port is arranged adjacent to the analysis port on the other side of the delivery port, a drain port is arranged adjacent to the injection port on the other side of the analysis port, and a syringe port is arranged adjacent to the drain port on the other side of the injection port. The rotor includes a first groove, a second groove, and a third groove for communicating, respectively, between the syringe pump and the drain port, between the delivery port and the sampling port, and between the analysis port and the injection port when the rotor is in an injecting position. The position of the rotor after the rotor is rotated from the injecting position in such a way that the third groove is moved to the drain port side and the injection port and the drain port are communicated by the third groove is a purging position. The second groove is provided as an arc-shaped groove that is longer than the arc between the delivery port and the sampling port on the circumference so as to maintain a state where the delivery port and the sampling port are communicated while the rotor is being rotated from the injecting position to the purging position.

As a specific example of the embodiment described above, the ports of the switching valve are arranged evenly on the circumference so that a space corresponding to an arc of 60 degrees of the circumference is present between adjacent ports, and the first groove is an arc-shaped groove of 60 degrees of the circumference, the second groove is an arc-shaped groove of 90 degrees of the circumference, which is provided being separate from one end of the first groove by a space corresponding to an arc of 30 degrees of the circumference, and the third groove is an arc-shaped groove of 90 degrees of the circumference, which is provided being separate from the other end of the first groove by a space corresponding to an arc of 30 degrees of the circumference. According to such a structure, the structure of the switching valve is simplified, and an increase in the cost may be suppressed, and also, since the rotor may simply be rotated at angles of 30 degrees, operation control of the switching valve is facilitated.

As a preferred example of a liquid chromatograph, an example where an analysis operation management section for performing a series of analysis operation by controlling the delivery device and the autosampler is provided, may be cited. In such an example, the analysis operation management section performs a series of analysis operation by performing the following operations in the specified order:

(1) a sampling operation of inserting a needle into a sample container in a state where the rotor of the switching valve is in the loading position, and taking in an analysis target sample by the syringe pump and causing the sample to be retained in a sample loop, (2) an injecting operation of inserting, after the sampling operation, a needle tip into the injection port, placing the rotor of the switching valve in the injecting position, and introducing the sample retained in the sample loop into the analysis channel, (3) a first purge operation of placing, after the injecting operation is completed, the rotor of the switching valve in the purging position in a state where the needle tip is inserted in the injection port, and delivering, from the delivery device, a mobile phase with components in an initial state in gradient analysis to replace the mobile phase in the sampling channel, and (4) a second purge operation of placing, after the first purge operation is completed, the rotor of the switching valve in the loading position, and delivering, from the delivery device, the mobile phase with the components in the initial state in gradient analysis to replace the mobile phase in the analysis channel.

Furthermore, if there is an analysis target sample following, the analysis operation management section performs the sampling operation of (1) on the next analysis target sample during the second purge operation of (4). Since sampling of the next analysis target sample is performed while the process of returning the components of the mobile phase in the analysis channel to the components in the initial state in the gradient analysis is being performed, the time from end of the injecting operation for a sample to the start of analysis of the next sample is reduced.

The analysis operation management section is desirably configured in such a way that the delivery flow rate of the delivery device during the first purge operation is higher than the delivery flow rate of the delivery device during the second purge operation. By separating the sampling channel whose channel resistance is smaller than that of the analysis channel from the analysis channel, it becomes possible to cause a mobile phase to flow in the sampling channel at a high flow rate, and thus, the delivery flow rate of the delivery device during the first purge operation may be made higher than the delivery flow rate of the delivery device during the second purge operation. The time required by the first purge operation is thus reduced, and the time until the start of analysis of the next sample is reduced.

An example of a liquid chromatograph provided with the autosampler will be described with reference to FIG. 1.

The liquid chromatograph includes a delivery device 2, an autosampler 4, a column oven 6, and a detector 8. The autosampler 4 is provided with a rotary switching valve 12 for switching the channel structure of the liquid chromatograph, and a channel from the delivery device 2 and an analysis channel 22 are connected to ports of the switching valve 12. An analytical column 24 and the detector 8 are provided, from the upstream side, on the analysis channel 22. The analytical column 24 is accommodated inside the column oven 6, and its temperature is adjusted to be constant.

The delivery device 2 includes two delivery pumps 10a and 10b for delivering two types of liquids (for example, water and acetonitrile), and a mixer 11 for mixing the liquids. The delivery device 2 is capable of gradient analysis according to which the mixing ratio (components) of the liquids at the mixer 11 changes with the lapse of time from the start of analysis. The outlet of the mixer 11 is connected to a port (6) of the switching valve 12 via a pipe.

The switching valve 12 of the autosampler 4 is a 6-port valve having six ports (1) to (6) evenly arranged on the same circumference. The port (1) is a sampling port to which a base end of a sampling channel 14 is connected. The port (2) is a syringe port to which a suction/discharge port of a syringe pump 17 is connected. The port (3) is a drain port to which a drain channel 18 leading to a drain is connected. The port (4) is provided with an injection port 20, and in the following, this port will be referred to as an injection port (4). The port (5) is an analysis port to which the analysis channel 22 is connected. The port (6) is a delivery port to which the delivery device 2 is connected.

The sampling channel 14 includes, at a tip portion, a needle 15 that is supported in a movable manner, and also includes a sample loop 16 for retaining a liquid taken in from the tip of the needle 15. Although not shown, the autosampler 4 includes a drive mechanism for driving the needle 15 in the horizontal plane direction and the vertical direction, and is capable of moving the needle 15 to the position of a sample container containing an analysis target sample, the position of the injection port 20, and the position of a cleaning port for cleaning the inner and outer surfaces of the needle 15.

The switching valve 12 switches connections between adjacent ports by rotating a rotor (not shown). The rotor of the switching valve 12 is provided with a first groove 13a, a second groove 13b and a third groove 13c as grooves for communicating between adjacent ports. These grooves 13a, 13b and 13c are arc-shaped grooves that are moved by rotation of the rotor, along the circumference where the ports (1) to (6) are provided.

The first groove 13a is a groove formed into an arc of 60 degrees of the circumference where the ports (1) to (6) are provided, and the second groove 13b and the third groove 13c are grooves formed into an arc of 90 degrees of the circumference. The second groove 13b is provided being separate from an end of the first groove 13a in the counter-clockwise direction (in FIG. 1) by an arc of 30 degrees, and the third groove 13c is provided being separate from an end of the first groove 13a in the clockwise direction (in FIG. 1) by an arc of 30 degrees. A space corresponding to an arc of 60 degrees is provided between the second groove 13b and the third groove 13c. According to such a structure, the rotor of the switching valve 12 may be placed in the following three positions (A) to (B).

Figure 2:
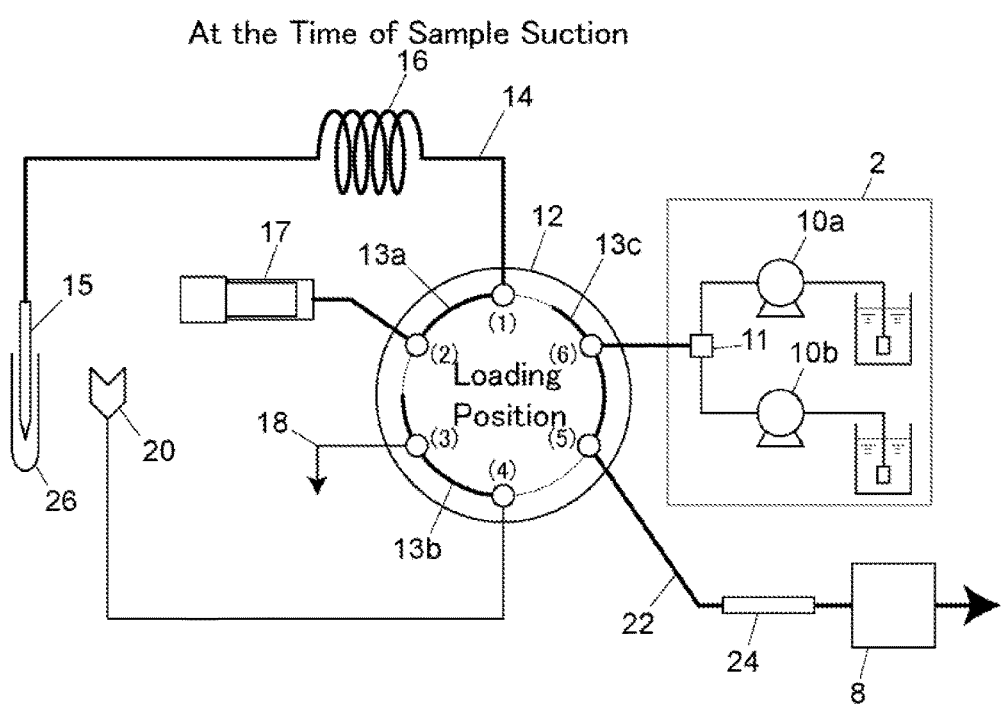
FIG. 2 is a channel structure diagram showing a state at the time of suction of a sample according to the present example.

(A) Loading Position (See FIG. 2)

The loading position is a position in which the sampling port (1) and the syringe port (2) are communicated by the first groove 13a, the drain port (3) and the injection port (4) are communicated by the second groove 13b, and the analysis port (5) and the delivery port (6) are communicated by the third groove 13c. As shown by a thick line in FIG. 2, when the rotor is placed in this loading position, the syringe pump 17 and the needle 15 are communicated, and suction of a sample via the needle 15 (the sampling operation) is enabled. Also, the mobile phase from the delivery device 2 is supplied to the analysis channel 22 through the groove 13c.

Figure 3:
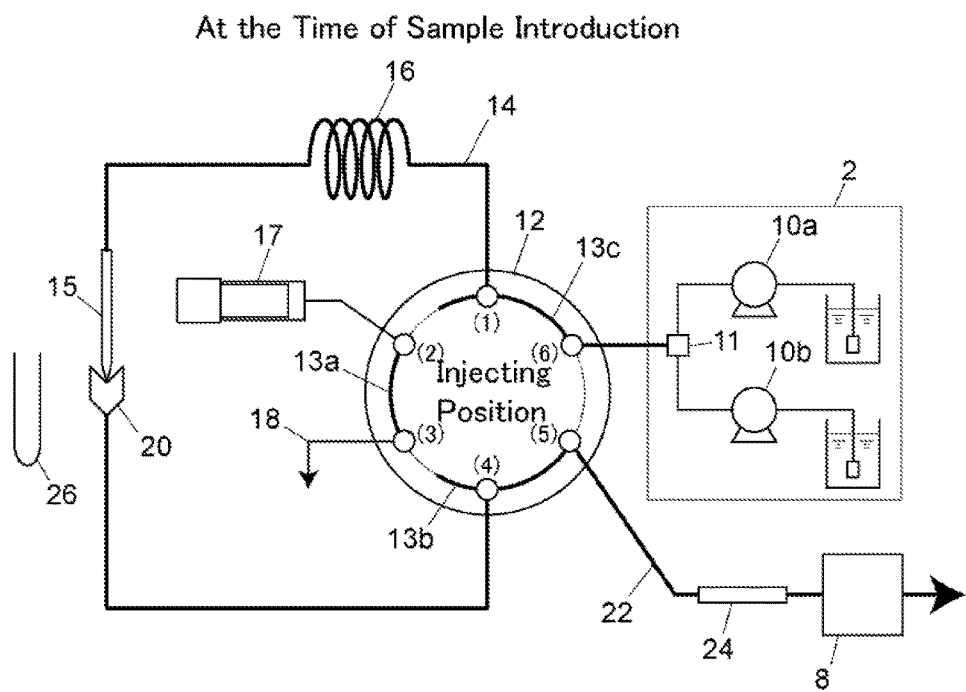
FIG. 3 is a channel structure diagram showing a state at the time of introduction of a sample according to the present example.

(B) Injecting Position (See FIG. 3)

The injecting position is a position in which the sampling port (1) and the delivery port (6) are communicated by the third groove 130, and the injection port (4) and the analysis port (5) are communicated by the second groove 13b. As shown by a thick line is FIG. 3, by inserting the needle 15 in the injection port 20, and placing the rotor in the injecting position, a channel is formed by which the mobile phase from the delivery device 2 is supplied to the analysis channel 22 through the third groove 13c, the sampling channel 14, the injection port 20, and the second groove 13b.

By forming this channel after the sampling operation shown in FIG. 2 is completed, the injection operation of introducing, into the analysis channel 22, a sample which is retained in the sample loop 16 due to the mobile phase from the delivery device 2 may be performed. A sample is introduced into the analytical column 24 by this injecting operation and is separated into components, and the separated sample components are further introduced into the detector 8 and are detected.

Additionally, when the rotor of the switching valve 12 is in the injecting position, the syringe port (2) and the drain port (3) are communicated by the first groove 13a, and an operation such as suction of a cleaning liquid by the syringe pump 17 may also be performed during the injecting operation.

Figure 4:
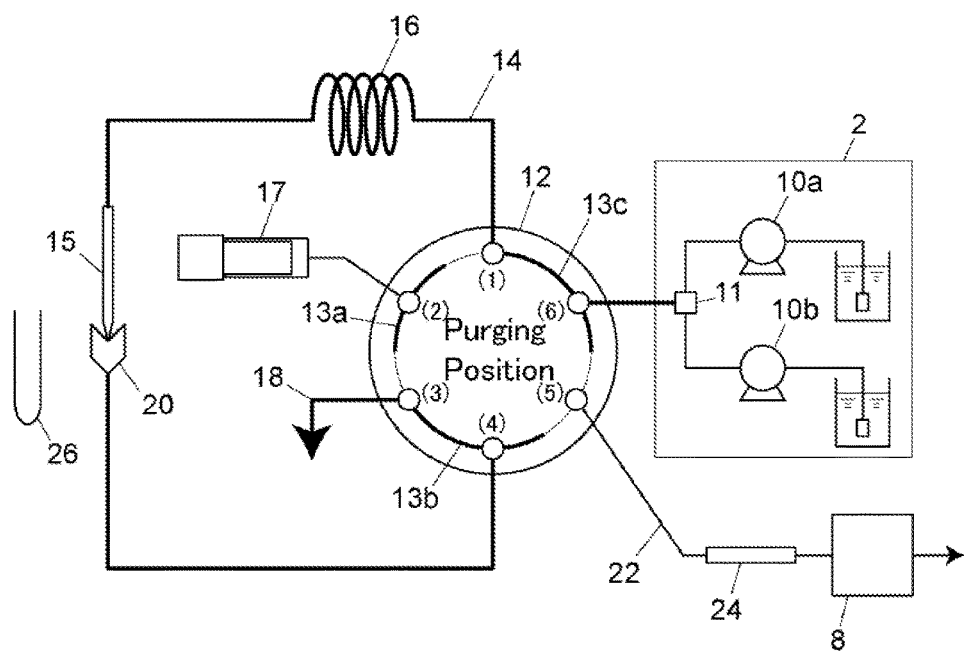
FIG. 4 is a channel structure diagram showing a state at the time of execution of fast purge according to the present example.

(C) Purging Position (see FIG. 4)

The purging position is a position in which the sampling port (1) and the delivery port (6) are communicated by the third groove 13c, and the injection port (4) and the drain port (3) are communicated by the second groove 13b. As shown by a thick line in FIG. 4, by inserting the needle 15 in the injection port 20, and placing the rotor in the purging position, the mobile phase from the delivery device 2 is discharged to the drain through the third groove 13c, the sampling channel 14, the injection port 20, the second groove 13b, and the drain channel 18.

By forming this channel after the injecting operation in FIG. 3 is completed, a purge process for the mobile phase in the channel may be singularly performed by the sampling channel 14, separately from the analysis channel 22.

The purge process here refers to a process of replacing, after analysis of a sample by a gradient method is completed, the mobile phase with components in the final state of the gradient analysis remaining in the channel by a mobile phase with components in the initial state. In the following, performance of the purge process for the mobile phase in the sampling channel 14 will be referred to as the first purge operation, and performance of the purge process for the mobile phase in the analysis channel 22 will be referred to as the second purge operation.

According to this liquid chromatograph, by including the three positions mentioned above for the rotor of the switching valve 12, the purge process for the mobile phase in the channel after completion of the injecting operation may be performed in two stages for the sampling channel 14 and the analysis channel 22, respectively. Since the channel resistance of the sampling channel 14 is smaller than that of the analysis channel 22, a mobile phase may be delivered from the delivery device 2 at a high flow rate in the first purge operation, and thus, the mobile phase in the sampling channel 14 may be swiftly replaced. Moreover, if the rotor of the switching valve 12 is switched to the loading position after the first purge operation is completed, the second purge operation of replacing the mobile phase in the analysis channel 22 may be performed, and, as well, the needle 15 may be moved to the position of a sample container 26 during the second purge operation and the sampling operation of the next sample may be performed.

A 6-way valve that is generally used by a conventional autosampler has only two positions of the loading position and the injecting position, and the mobile phases in the sampling channel and the analysis channel are replaced at the same time. Accordingly, since the mobile phases cannot be made to flow at a high flow rate, the replacement process for the mobile phases takes a long time, and also, during this process, sampling of the next sample cannot be performed.

Figure 5:
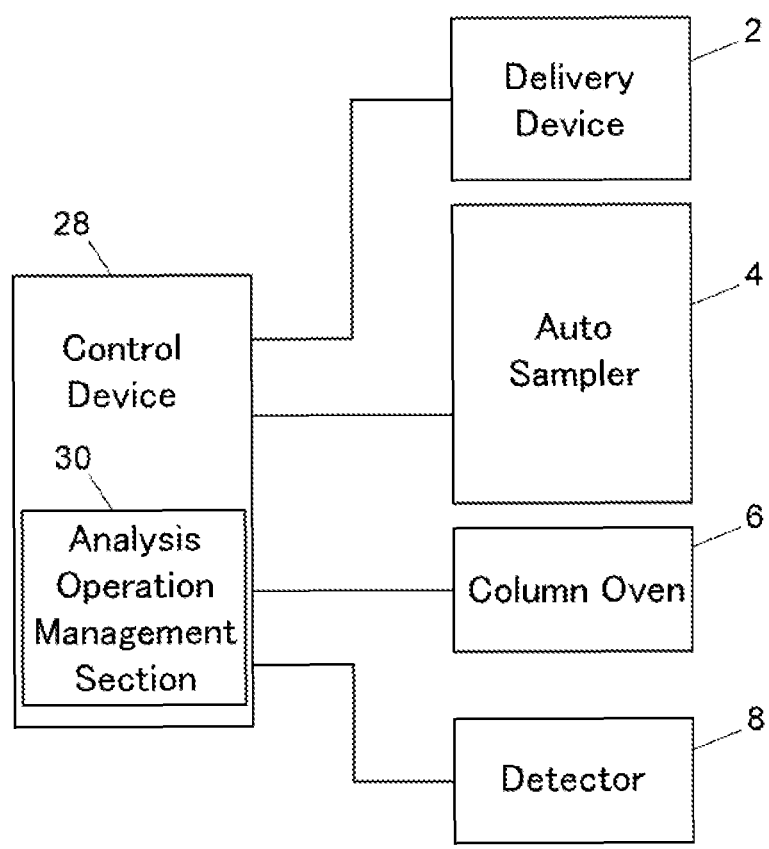
FIG. 5 is a block diagram showing a control system according to the present example.

FIG. 5 is a diagram showing an example of an overall control system of the liquid chromatograph. The delivery device 2, the autosampler 4, the column oven 6, and the detector 8 are modularized respectively, and each module is capable of communicating information by a communication cable with, for example, a control device 28, which is configured by a system controller or a general-purpose personal computer. The operations of the delivery device 2, the autosampler 4, and the column oven 6 are managed in a centralized manner by the control device 28. Also, a detection signal obtained by the detector 8 is captured into the control device 28.

The control device 28 is provided with an analysis operation management section 30 for performing a series of analysis operation by managing respective operations of the modules. The analysis operation management section 30 is a function that is realized by a program stored in a storage device of the control device 28 along with an arithmetic element (CPU) and the like for executing the program.

An example of the series of analysis operation to be performed by the analysis operation management section 30 of the control device 28 will be described with reference to FIG. 1 and the flow chart in FIG. 6.

First, to perform the sampling operation of a sample, the rotor of the switching valve 12 is placed in the loading position (see FIG. 2), the needle 15 is moved to the position of the sample container 26 containing an analysis target sample, and the sample is taken in by driving the syringe pump 17 to perform suction. The sample taken in from the tip of the needle 15 is retained in the sample loop 16. Additionally, the channel from the syringe pump 17 to the tip of the needle 15 is filled, in a stage preceding start of the sampling operation, by a mobile phase with components in the initial stage of the gradient analysis.

After the sampling operation is completed, the needle 15 is moved to the position of the injection port 20, the tip of the needle 15 is inserted into the injection port 20, and then the rotor of the switching valve 12 is switched to the injecting position (see FIG. 3). Then, the gradient analysis of changing over time the components of the mobile phase that is delivered from the delivery device 2 is started. The sample that is retained in the sample loop 16 is thereby introduced into the analysis channel 22, is separated into components by the analytical column 24, and each sample component is detected by the detector 8.

When the series of the gradient analysis is completed, the rotor of the switching valve 12 is switched to the purging position (see FIG. 4), and the mobile phase with the components in the initial state in the gradient analysis is delivered from the delivered device 2 at a flow rate (for example, 5 ml/min) higher than the flow rate (for example, 1 ml/min) at the time of analysis. The mobile phase, in the sampling channel 14, with components in the final state in the gradient analysis is thereby swiftly replaced by the mobile phase with the components in the initial state in the gradient analysis (the first purge operation).

After the first purge operation is completed, the rotor of the switching valve 12 is switched to the loading position (see FIG. 2), and the mobile phase with the components in the initial state in the gradient analysis is supplied into the analysis channel 22, replacing the mobile phase in the analysis channel 22 (the second purge operation). In the case where there is a sample to be analyzed next, the sampling operation is performed for the next sample during the second purge operation, and the injecting operation for the sample is performed after the second purge operation is completed. In the case where there is no sample to be analyzed next, the series of analysis operation is completed after the end of the second purge operation.

What is claimed is:

1. An autosampler comprising:
    a sampling channel including, at a tip, a movable needle for performing suction and discharge of a sample, and also including a sample loop for retaining a liquid taken in from the needle tip; and
    a switching valve including a delivery port to which a delivery device for delivering a mobile phase is connected, a sampling port to which a base end of the sampling channel is connected, an injection port that is connected to the sampling channel by insertion of the tip of the needle, an analysis port to which an analysis channel provided with an analytical column is connected, a drain port that leads to a drain, and a rotor including multiple grooves for communicating between the ports, the switching valve being for switching a connection state between the ports by switching a position by rotating the rotor,
    wherein the rotor includes an injecting position in which the delivery port and the sampling port are communicated and the injection port and the analysis port are communicated, a purging position in which the delivery port and the sampling port are communicated and the injection port and the drain port are communicated, and a loading position in which the delivery port and the analysis port are communicated,
    wherein the purging position is a position for replacing mobile phase in the sampling channel separately from the analysis channel by discharging mobile phase sent by the delivery device to the drain through the sampling channel, the injection port, and the drain port.

2. The autosampler according to claim 1, further comprising
    a syringe pump for performing suction and discharge of a liquid,
    wherein the switching valve includes a syringe port that leads to the syringe pump, and when the rotor is in the loading position, the sampling port and the syringe port are communicated.

3. The autosampler according to claim 2,
    wherein the ports of the switching valve are arranged on a same circumference, the delivery port and the syringe port are adjacent to the sampling port, the analysis port is adjacent to the delivery port on the other side of the sampling port, the injection port is adjacent to the analysis port on the other side of the delivery port, the drain port is adjacent to the injection port on the other side of the analysis port, and the syringe port is adjacent to the drain port on the other side of the injection port,
    wherein the rotor includes a first groove, a second groove, and a third groove for communicating, respectively, between the syringe pump and the drain port, between the delivery port and the sampling port, and between the analysis port and the injection port when the rotor is in the injecting position,
    wherein a position of the rotor after the rotor is rotated from the injecting position in such a way that the third groove is moved to the drain port side and the injection port and the drain port are communicated by the third groove is a purging position, and wherein the second groove is provided as an arc-shaped groove that is longer than an arc between the delivery port and the sampling port on the circumference so as to maintain a state where the delivery port and the sampling port are communicated while the rotor is being rotated from the injecting position to the purging position.

4. The autosampler according to claim 3,
wherein the ports of the switching valve are arranged evenly on the circumference so that a space corresponding to an arc of 60 degrees of the circumference is present between adjacent ports,
wherein the first groove is an arc-shaped groove of 60 degrees of the circumference,
wherein the second groove is an arc-shaped groove of 90 degrees of the circumference, the second groove being provided being separate from one end of the first groove by a space corresponding to an arc of 30 degrees of the circumference, and
wherein the third groove is an arc-shaped groove of 90 degrees of the circumference, the third groove being provided being separate from an other end of the first groove by a space corresponding to an arc of 30 degrees of the circumference.

5. A liquid chromatograph comprising:
an analysis channel including an analytical column for separating a sample into components, and a detector for detecting a sample component separated by the analytical column;
a delivery device for supplying a mobile phase to the analysis channel; and
an autosampler, present between the delivery device and the analysis channel, for introducing a sample into the analysis channel, the autosampler comprising:
 a sampling channel including, at a tip, a movable needle for performing suction and discharge of a sample, and also including a sample loop for retaining a liquid taken in from the needle tip; and
 a switching valve including a delivery port to which a delivery device for delivering a mobile phase is connected, a sampling port to which a base end of the sampling channel is connected, an injection port that is connected to the sampling channel by insertion of the tip of the needle, an analysis port to which an analysis channel provided with an analytical column is connected, a drain port that leads to a drain, and a rotor including multiple grooves for communicating between the ports, the switching valve being for switching a connection state between the ports by switching a position by rotating the rotor, wherein the rotor includes an injecting position in which the delivery port and the sampling port are communicated and the injection port and the analysis port are communicated, a purging position in which the delivery port and the sampling port are communicated and the injection port and the drain port are communicated, and a loading position in which the delivery port and the analysis port are communicated,
wherein the purging position is a position for replacing mobile phase in the sampling channel separately from the analysis channel by discharging mobile phase sent by the delivery device to the drain through the sampling channel, the injection port and the drain port.

6. The liquid chromatograph according to claim 5, further comprising an analysis operation management section for performing a series of analysis operation by controlling the delivery device and the autosampler,
wherein the analysis operation management section performs in order
 (1) a sampling operation of inserting a needle into a sample container in a state where a rotor of the switching valve is in a loading position, and taking in an analysis target sample by the syringe pump and causing the sample to be retained in the sample loop,
 (2) an injecting operation of inserting, after the sampling operation, the needle tip into the injection port, placing the rotor of the switching valve in the injecting position, and introducing the sample retained in the sample loop into the analysis channel,
 (3) a first purge operation of placing, after the injecting operation is completed, the rotor of the switching valve in the purging position in a state where the needle tip is inserted in the injection port, and delivering, from the delivery device, a mobile phase with a component in an initial state in gradient analysis to replace a mobile phase in the sampling channel, and
 (4) a second purge operation of placing, after the first purge operation is completed, the rotor of the switching valve in the loading position, and delivering, from the delivery device, the mobile phase with the component in the initial state in gradient analysis to replace a mobile phase in the analysis channel, and
wherein, if there is a next analysis target sample, the sampling operation of (1) is performed on the next analysis target sample during the second purge operation of (4).

7. The liquid chromatograph according to claim 6, wherein the analysis operation management section is configured in such a way that a delivery flow rate of the delivery device during the first purge operation is higher than a delivery flow rate of the delivery device during the second purge operation.

* * * * *